(12) United States Patent
Payet-Burin

(10) Patent No.: US 10,376,467 B2
(45) Date of Patent: Aug. 13, 2019

(54) PROCESS FOR RECONSTITUTION OF A SOLID FORM OF A PHARMACEUTICAL COMPOSITION

(71) Applicants: UCB BIOPHARMA SPRL, Brussels (BE); EVEON, Montbonnot-Saint-Martin (FR)

(72) Inventor: Xavier Payet-Burin, Villard Bonnot (FR)

(*) Notice: Subject to any disclaimer, the term of this patent is extended or adjusted under 35 U.S.C. 154(b) by 300 days.

(21) Appl. No.: 15/112,046

(22) PCT Filed: Jan. 20, 2015

(86) PCT No.: PCT/EP2015/050988
§ 371 (c)(1),
(2) Date: Jul. 15, 2016

(87) PCT Pub. No.: WO2015/107214
PCT Pub. Date: Jul. 23, 2015

(65) Prior Publication Data
US 2016/0331682 A1    Nov. 17, 2016

(30) Foreign Application Priority Data
Jan. 20, 2014 (EP) .................................... 14305070

(51) Int. Cl.
*A61K 9/19* (2006.01)
*A61K 9/00* (2006.01)
*A61K 47/60* (2017.01)

(52) U.S. Cl.
CPC .............. *A61K 9/0095* (2013.01); *A61K 9/19* (2013.01); *A61K 47/60* (2017.08)

(58) Field of Classification Search
CPC ......... A61K 9/0095; A61K 9/19; A61K 47/60
(Continued)

(56) References Cited

U.S. PATENT DOCUMENTS

| 4,543,101 A | 9/1985 | Crouch |
| 4,741,900 A | 5/1988 | Alvarez et al. |

(Continued)

FOREIGN PATENT DOCUMENTS

| JP | 2008512193 | 4/2008 |
| WO | WO 98/25971 | 6/1998 |

(Continued)

OTHER PUBLICATIONS

Bansal et al., "Variable Affecting Reconstitution Time of Dry Powder for Injection," Pharmaceutical Technology, Jul. 2, 2008, vol. 32, Issue 7, pp. 1-6.
(Continued)

*Primary Examiner* — David L Sorkin
(74) *Attorney, Agent, or Firm* — McDonnell Boehnen Hulbert & Berghoff LLP

(57) ABSTRACT

The invention relates to a process for reconstitution of a solid form of a pharmaceutical composition, comprising the following successive steps: (i) providing the solid form of the pharmaceutical composition in a sealed container, the pressure within the container being an initial pressure ($p_i$,) comprised between 0.5 Pa and $1.2 \times 10^5$ Pa; (ii) at a first time point ($t_0$) introducing the solvent into said sealed container and maintaining the resulting pressure ($p_r$) within the container during a controlled time $\Delta t_1$; and (iii) at a second time point ($t_2$) increasing the pressure within the container to a controlled pressure ($p_2$) higher than said resulting pressure ($p_r$) until complete reconstitution.

19 Claims, 8 Drawing Sheets

(58) Field of Classification Search
USPC .......................................................... 366/139
See application file for complete search history.

(56) References Cited

U.S. PATENT DOCUMENTS

| | | | |
|---|---|---|---|
| 5,219,996 | A | 6/1993 | Bodmer et al. |
| 5,667,425 | A | 9/1997 | Pineau et al. |
| 6,307,026 | B1 | 10/2001 | King et al. |
| 7,891,076 | B2* | 2/2011 | Schmitt ................. B05C 13/025 |
| | | | 242/571.1 |
| 7,981,076 | B2 | 7/2011 | Sullivan et al. |
| 8,454,833 | B2* | 6/2013 | Nikolic .................... A61K 9/08 |
| | | | 210/651 |
| 2004/0005310 | A1 | 1/2004 | Rapp et al. |
| 2011/0155620 | A1 | 6/2011 | Kuu |
| 2013/0216541 | A1* | 8/2013 | Dali ................... C07K 16/2827 |
| | | | 424/134.1 |
| 2014/0005636 | A1* | 1/2014 | Wang .................... A61M 5/284 |
| | | | 604/518 |

FOREIGN PATENT DOCUMENTS

| | | |
|---|---|---|
| WO | 00/07539 | 2/2000 |
| WO | WO 04/72116 | 8/2004 |
| WO | WO 2013/098805 | 7/2013 |

OTHER PUBLICATIONS

Transmittal of International Search Report and Written Opinion of International Searching Authority for International Application No. PCT/EP2015/050988 filed Jan. 20, 2015, 8 pages.

* cited by examiner

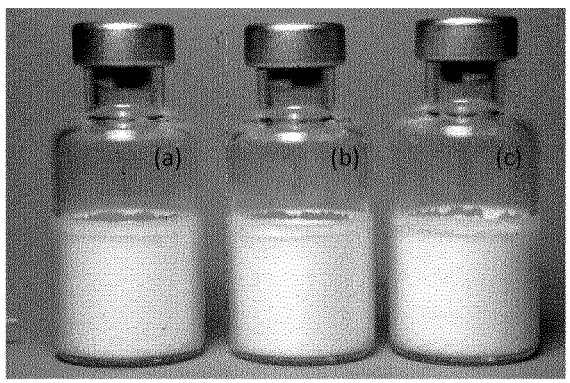
FIGURE 6A $t_0$
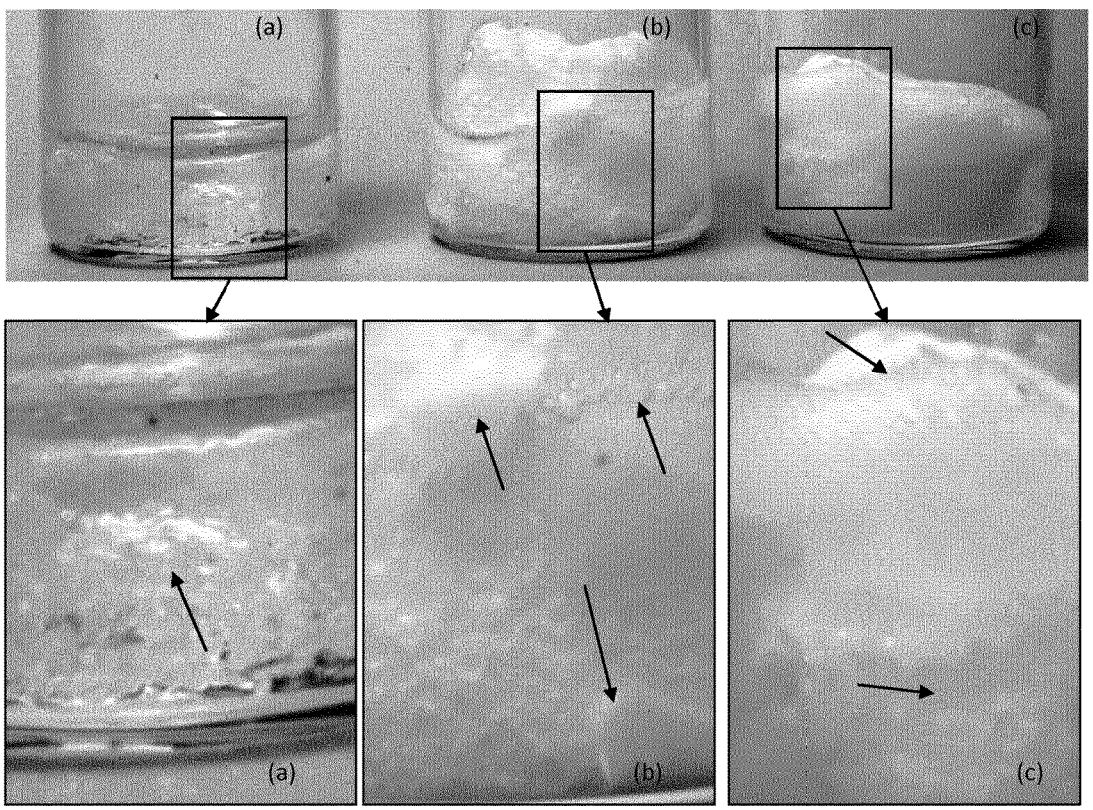
FIGURE 6B $t_0$+1min
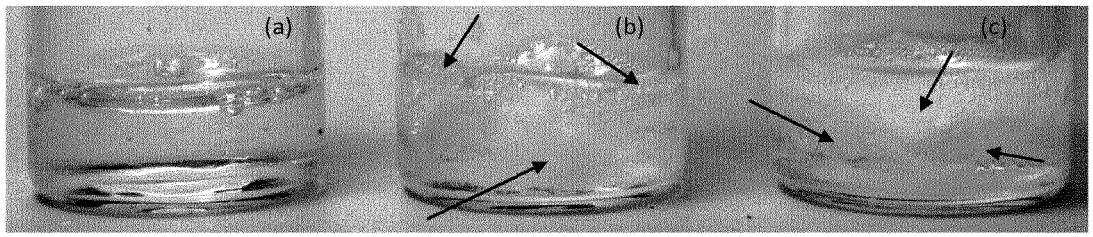
FIGURE 6C $t_0$+4min

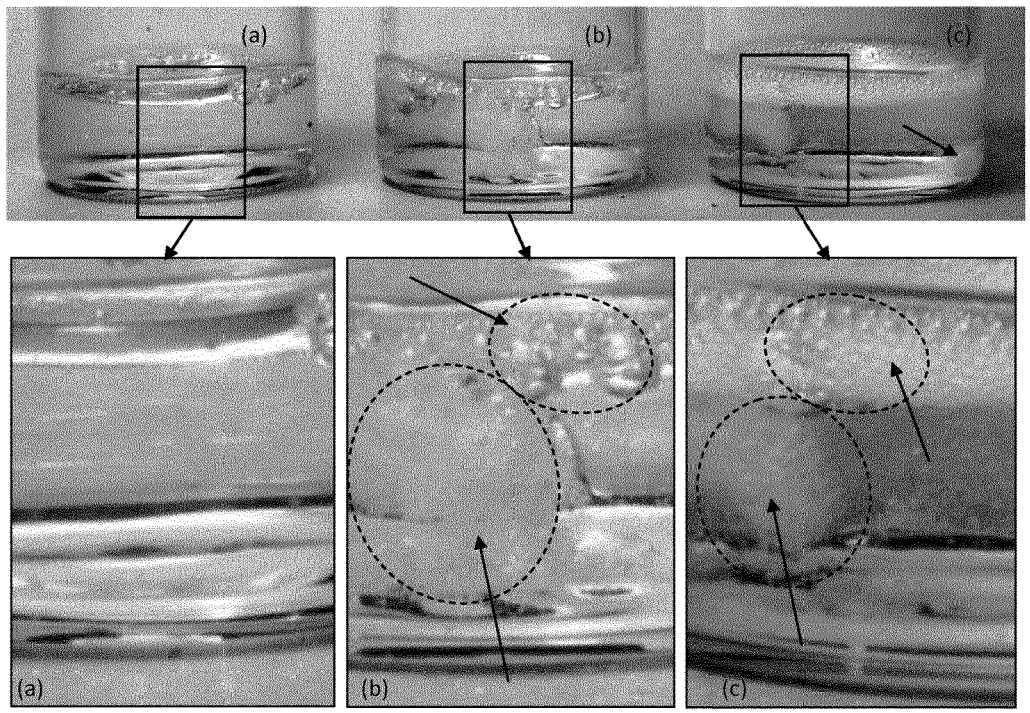
FIGURE 6D $t_0+10min$
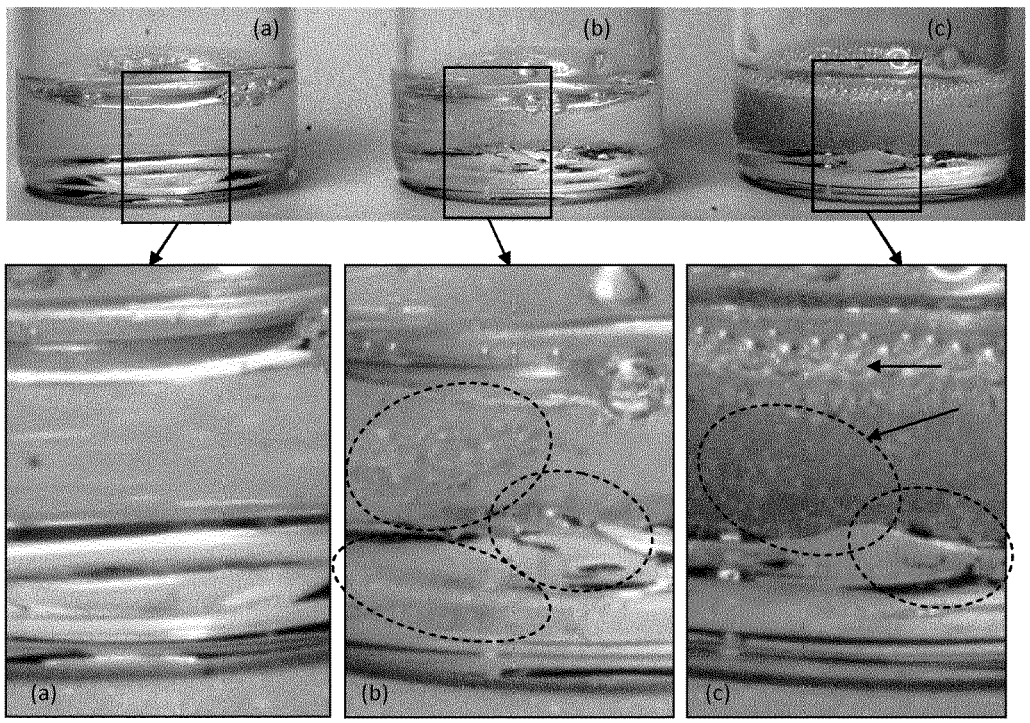
FIGURE 6E $t_0+20min$

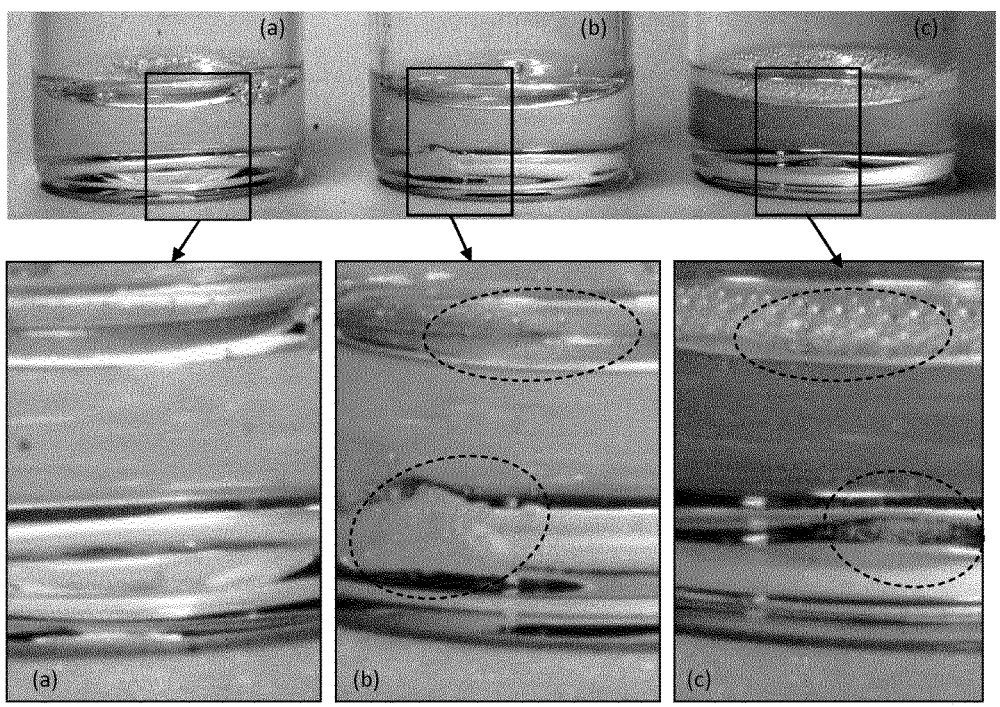
FIGURE 6F $t_0+25$min

PROCESS FOR RECONSTITUTION OF A SOLID FORM OF A PHARMACEUTICAL COMPOSITION

This application is the US national phase under 35 U.S.C. § 371 of international application PCT/EP2015/050988, filed Jan. 20, 2015, which claims priority to EP application 14305070.6, filed Jan. 20, 2014.

FIELD OF THE INVENTION

The invention relates to a process for reconstitution of a solid form of a pharmaceutical composition.

BACKGROUND OF THE INVENTION

Certain types of pharmaceutically active ingredients cannot be administered orally due to subsequent alterations by the digestive system, and are thus generally administered parentally, e.g. intravenously or subcutaneously. In such a case, these pharmaceutically active ingredients have to be administered in liquid form. This is particularly the case for antibodies and other proteins that are large and complex molecules, as well as for certain chemical entities. However, antibodies and other large pharmaceutically active ingredients frequently have a poor stability in an aqueous environment, which may reduce the shelf life of the pharmaceutical composition to an unacceptable value.

Hence, it may be more advantageous in terms of stability, storage, and ease of shipping to prepare a solid form of the pharmaceutical composition, which may be reconstituted with a solvent shortly before its administration to a patient. Solid forms of pharmaceutical compositions that have to be administered in liquid form, e.g. through injection, are to be extemporaneously dissolved using an acceptable solvent composition to produce a solution for injection. Solid forms of pharmaceutical compositions include powders, freeze-dried (or lyophilized) compositions, spray-dried, spray-freeze dried, vacuum dried or supercritical fluid dried compositions.

The reconstitution steps may be carried out by the patient, a relative, a nurse or a healthcare professional, depending on the complexity of the reconstitution process. Typically it is preferable to use reconstitution processes which are relatively simple, reproducible and so would not require the presence of a healthcare professional. This is particularly true in cases of treatment of chronic diseases.

Although such reconstitution may be straightforward and as short as a few seconds for some specific compositions, it may take up to tens of minutes to reconstitute some others. Long reconstitution times involving complicated series of steps often lead to lower compliance with said protocols, and so finally can result in administration of a wrong dose and even potentially affect the outcome of the treatment.

Such hard and/or long to reconstitute solids generally have in common a poor wettability with respect to the solvent and/or a high final viscosity. Other frequent problems are the formation of foam, bubbles, creating a crown at the surface of the reconstituted pharmaceutical composition, gels or poorly wettable aggregates that require more time and attention for a careful reconstitution.

This is particularly the case for pharmaceutical compositions comprising high concentrations of large molecules, such as but not limited to monoclonal antibodies, polyclonal antibodies, certain recombinant proteins or polypeptides, steroid hormones and some large chemical entities such as antibiotics. It is also the case when the reconstitution is performed using less solvent volume than was originally taken out during processing towards a solid form, as is a common practice with formulations for injection so as to minimize the volume to be administered.

One can refer in this regard to the article by Pradip Hiwale et al. [1] which describes factors affecting reconstitution time of dry powder for injection and classifies them as intrinsic and extrinsic parameters.

In any case the most conventional manual process for reconstitution of a solid form of a pharmaceutical composition typically requires the following steps: retrieving the solvent from a first container, injecting it in a second container which contains the solid form of the pharmaceutical composition, homogenizing the liquid in the second container such that it is free of foam and/or dry aggregates, and withdrawing the reconstituted pharmaceutical composition from the second container for administration.

Each of these above-mentioned steps themselves may require several object manipulations, including needles or spikes, and the accomplishment of a defined process.

Depending on the manipulation steps applied and on the pharmaceutical composition, the reconstitution process may lead to a long reconstitution time, the presence of trapped dry lumps or gel zones that can hardly be reached by the solvent, the presence of trapped air bubbles or foaming, either in full volume or only limited to a ring at the air/liquid interface, and/or great variations in reconstitution times, each of which may be inacceptable for the reconstitution of the pharmaceutical composition.

In order to ensure the correct reconstitution and to reduce the user-to-user reconstitution deviations for pharmaceutical compositions, drug manufacturers provide users with an "Instructions for Use" leaflet to guide them in the process of reconstitution.

In most cases, the process includes a common solvent transfer phase, and for the homogenization several interwoven agitation/swirl and settling steps to wet the solid and observation of rehydration until complete dissolution is achieved, prior to final withdrawal. There may be recommendations of things "to do", or "not to do".

In addition, drug manufacturers may recommend a training for the user, may he/she be a professional or a patient or a relative or even limit the reconstitution to professionals.

For some lyophilized pharmaceutical compositions full reconstitution time may take as long as 30 minutes.

US 2011/0155620 describes that high or medium vacuum pressure (e.g. 100 Pa to $6 \times 10^4$ Pa) in vials filled with powder of a pharmaceutical composition helps to stabilize the composition during storage, facilitates the drawing of the solvent during reconstitution, evidences container closure integrity, possibly speeds up the reconstitution process and limits the production of foam.

WO 00/07539 teaches that foaming can be reduced by equalizing the pressure within the container with atmospheric pressure before introducing the solvent into the container; in this way, the solvent enters the container with less force and at a lower velocity.

However, despite the above-mentioned techniques, it is considered that the reconstitution of pharmaceutical compositions for administration remains a challenge, with respect to time but also other features. Hence, there remains a need in the art to further improve reconstitution processes for solid forms of pharmaceutical compositions.

BRIEF DESCRIPTION OF THE INVENTION

A goal of the invention is to provide a process for reconstitution of a solid form of a pharmaceutical composition that is simpler than processes known in the art, that allows reconstituting in a reduced time, in a more reproducible fashion, and that limits the presence of insoluble solid or gel and/or bubbles in the liquid composition after reconstitution.

To that end, the invention provides a process for reconstitution of a solid form of a pharmaceutical composition, comprising the following successive steps:
  (i) providing the solid form of the pharmaceutical composition in a sealed container, the pressure within the container being at an initial pressure $p_i$ comprised between 0.5 Pa and $1.2 \times 10^5$ Pa;
  (ii) at a first time point $t_0$ introducing a solvent into said sealed container and maintaining the resulting pressure $p_r$ within the container during a controlled time $\Delta t_1$; and
  (iii) at a second time point $t_2$, increasing the pressure within the container to a controlled pressure greater than the said resulting pressure $p_r$ until complete reconstitution.

According to an embodiment, the process comprises, after step (ii) and/or after step (iii), mixing the solvent and the pharmaceutical composition.

According to an embodiment, said mixing is carried out by fluidic recirculation of the solvent and the pharmaceutical composition and/or by mechanical mixing.

According to an embodiment, said mechanical mixing of the solvent and the pharmaceutical composition is carried out by rotating the container while the container is tilted with respect to the vertical position.

Before step (i) the pressure within the container may be adjusted to said initial pressure $p_i$.

According to an embodiment, the initial pressure $p_i$ in the container is from 0.5 Pa to $5 \times 10^4$ Pa.

According to an embodiment, the pressure $p_2$ set in the container at step (iii) is from $1 \times 10^4$ Pa to $1.5 \times 10^6$ Pa.

According to an embodiment, the solid form of the pharmaceutical composition is a lyophilized form of the pharmaceutical composition.

Alternatively, the solid form of the pharmaceutical composition may be a powder.

According to an embodiment, the solvent is introduced in the container as a jet directed to the solid form of the pharmaceutical composition.

The process may further comprise an additional step (iv) wherein after reaching the controlled pressure $p_2$ in step (iii), the pressure within the container is further increased before complete reconstitution.

The process may further comprise an additional step (v) wherein after reaching the controlled pressure $p_2$ in step (iii), the container is subjected to multiple pressure cycles before complete reconstitution.

According to an embodiment, the initial pressure (pi) within the container in step (i) is from 0 to $6 \times 10^4$ Pa and the controlled time $\Delta t_1$ in step (ii) is from 10 seconds to 2 minutes. The process comprises, after step (iii), a step of mixing the solvent and the pharmaceutical composition by fluidic recirculation and/or mechanical mixing.

BRIEF DESCRIPTION OF THE DRAWINGS

Other features and advantages of the invention will be apparent from the detailed description that follows, based on the appended drawings wherein.

FIG. 2A illustrates an example of time frame for a reconstitution process according to an embodiment of the invention.

The reconstitution process is considered to begin at time $t_0$, which corresponds to the start of introduction of the solvent in the container.

Just before introduction of the solvent, the pressure within the container is the initial pressure $p_i$.

Said pressure may be the pressure within the container during its previous storage, referred to as storage pressure $p_s$.

Figure 2A:
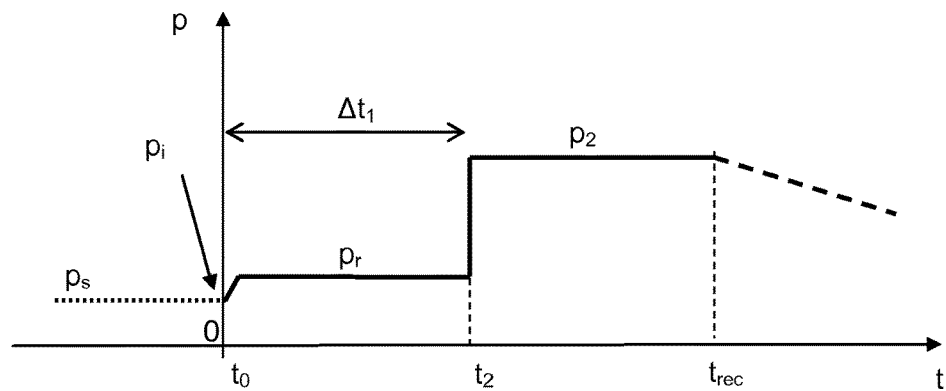
FIGS. 2A to 2D illustrate different embodiments of the process according to the present invention, wherein the x axis represents time and the y axis represents pressure within a container comprising the pharmaceutical composition. It is to be noted that although these graphs are drawn with linear segments, the variation of the pressure may vary in a non-linear manner, especially during the transitions between the different pressures involved during the reconstitution.
Figure 2B:
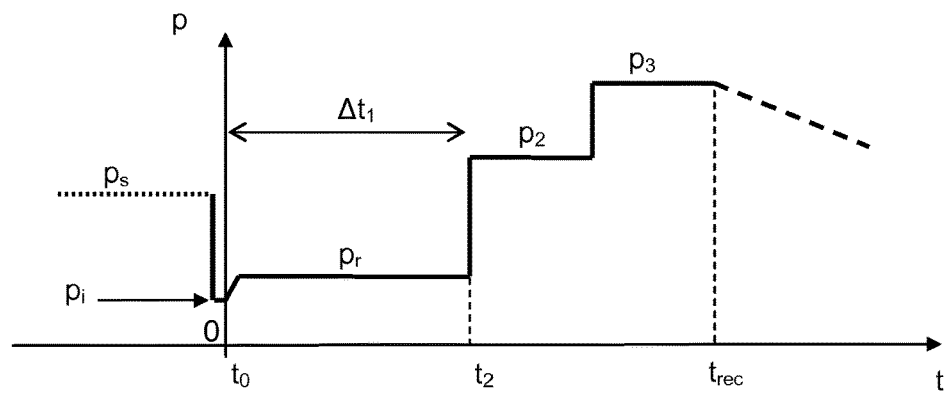

Alternatively, as illustrated in FIG. 2B, the pressure within the container during storage may be a pressure $p_s$ different (either greater or smaller) to $p_i$, and the pressure is set to $p_i$ a short time before beginning of the reconstitution process.

The introduction of the solvent in the container has the effect of slightly modifying the pressure; the resulting pressure is thus referred to as $p_r$.

This resulting pressure does not require to be quantified precisely; however, the resulting pressure $p_r$ has to be maintained during a defined time $\Delta t_1$.

At a defined time $t_2$ that corresponds to $t_0 + \Delta t_1$, which is a time when the reconstitution is not yet complete, the pressure within the container is increased to a pressure $p_2$ that is greater than $p_i$ and $p_r$.

The pressure within the container is maintained at pressure $p_2$ until complete reconstitution is observed (time $t_{rec}$). After time $t_{rec}$, the reconstituted composition may be retrieved from the container.

FIG. 2B illustrates an example of a time frame for a reconstitution process according to another embodiment of the invention.

As compared to the process of FIG. 2A, the process of FIG. 2B comprises an additional step of further increasing the pressure within the container to a pressure $p_3$, after a defined time at $p_2$ and before complete reconstitution of the pharmaceutical composition is observed.

Figure 2C:
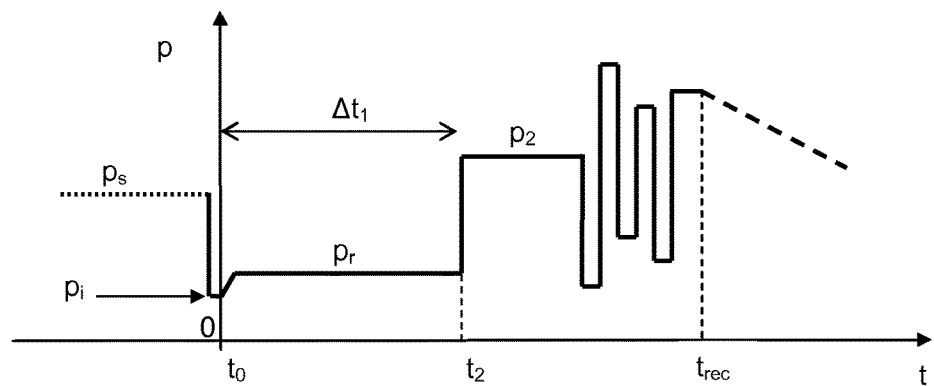

FIG. 2C illustrates an example of a time frame for a reconstitution process that comprises, after applying pressure $p_2$ and before applying pressure $p_3$, pressure cycles comprising successive pressure increases and decreases.

Figure 2D:
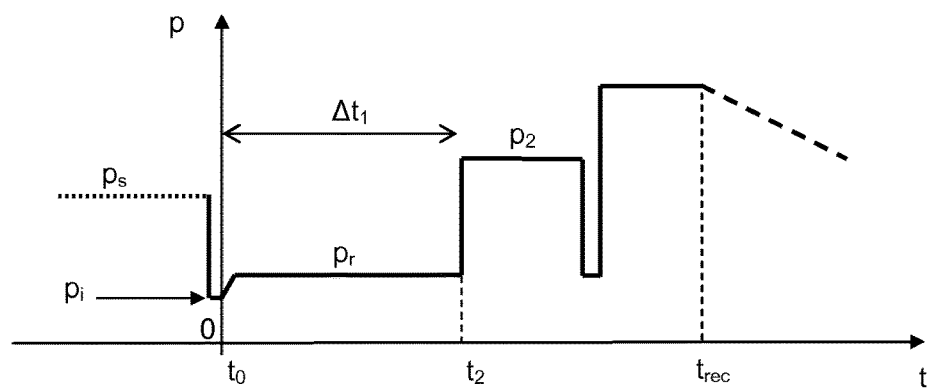

FIG. 2D illustrates a variation of the time frame shown in FIG. 2C comprising only one pressure decrease from pressure $p_2$ followed by a pressure increase to pressure $p_3$.

Figure 3:
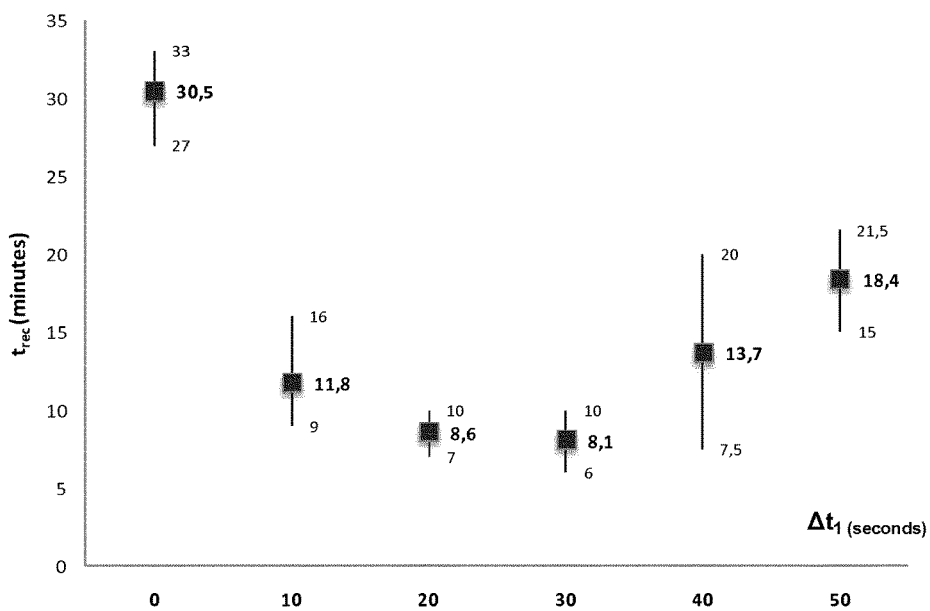
Figure 4A:
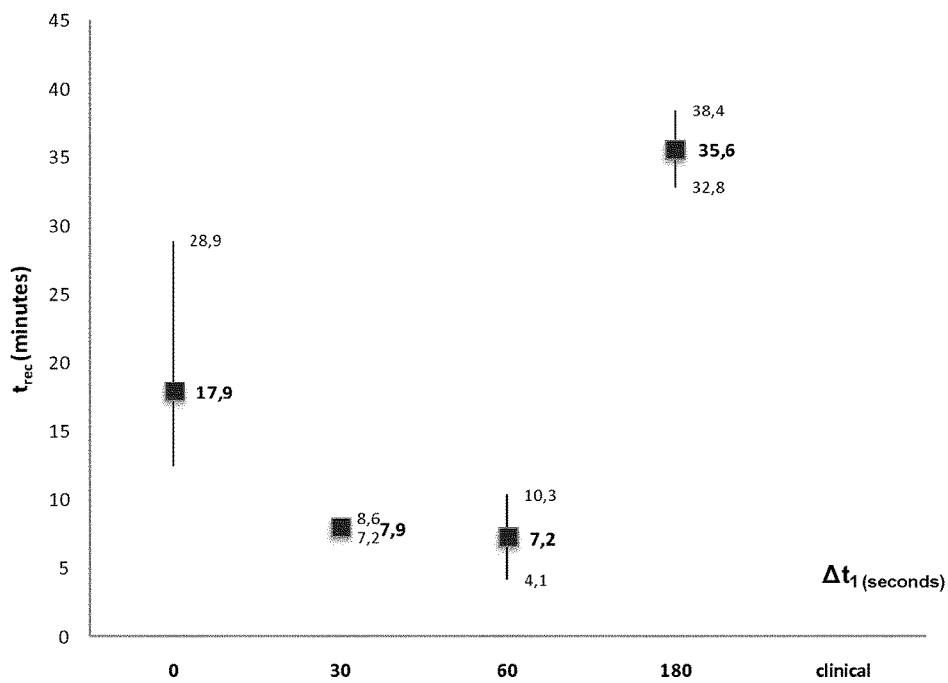
Figure 4B:
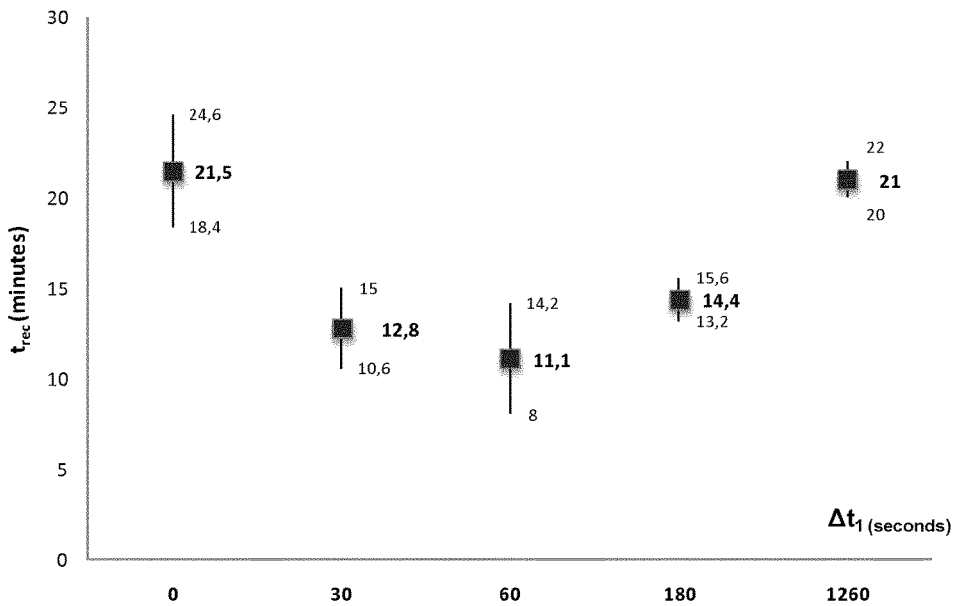
Figure 4C:
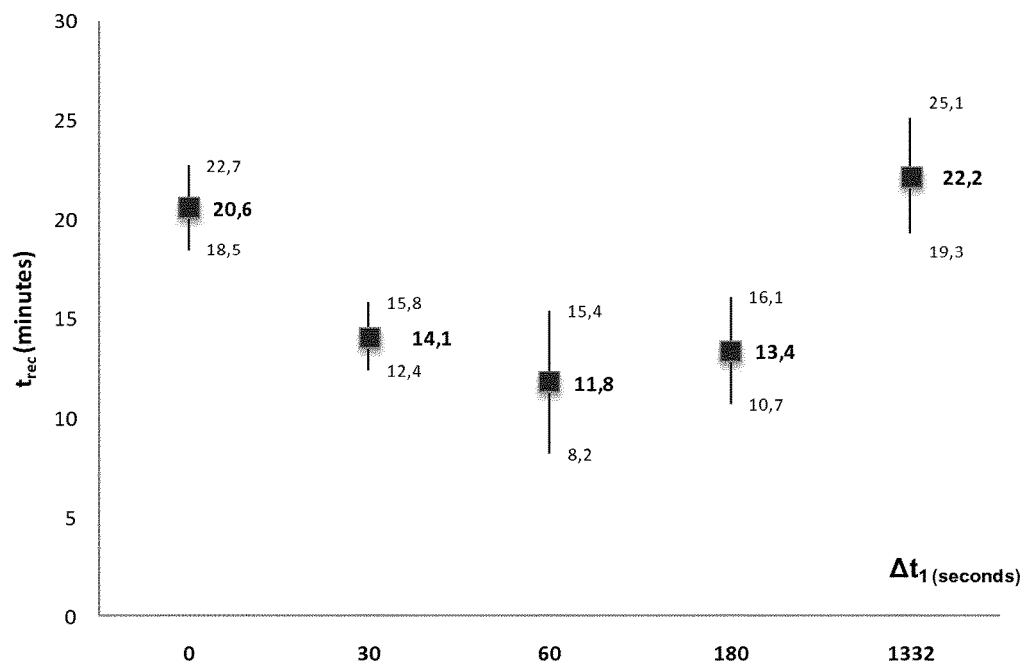
Figure 4D:
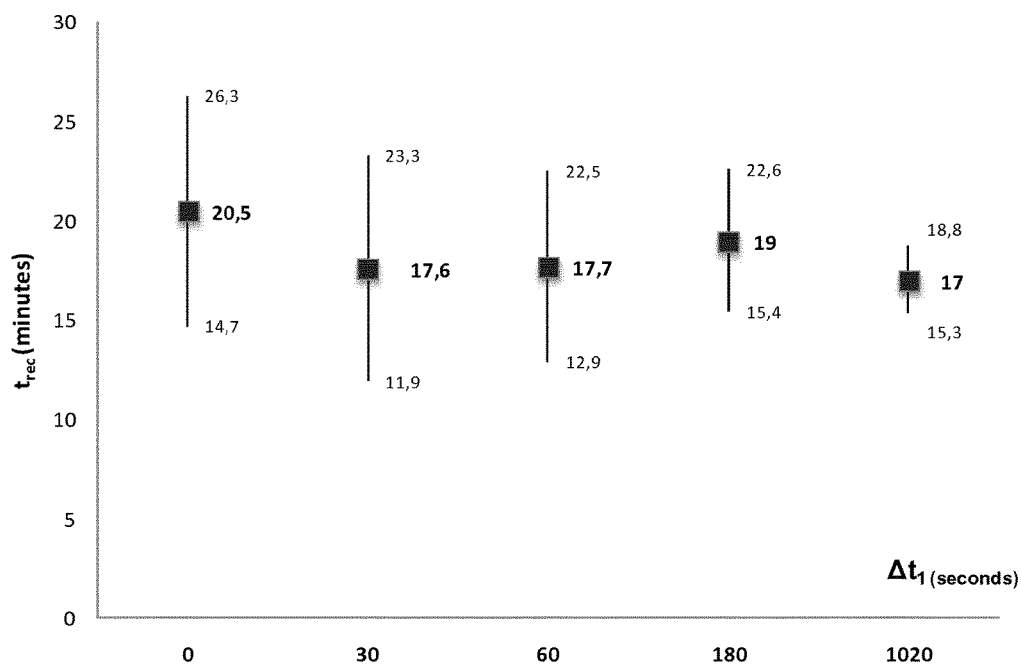
Figure 4E:
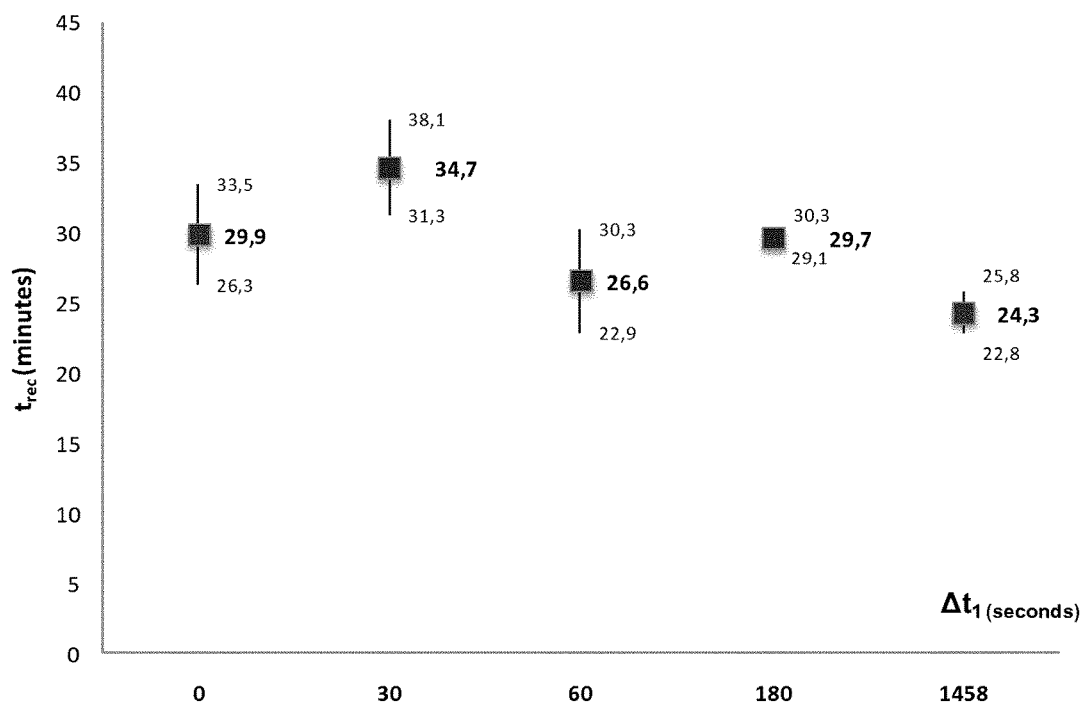

FIG. 3 illustrates the reconstitution times of a lyophilized formulation of a PEGylated fragment of an antibody (certolizumab pegol) with WFI as a function of the time during which the resulting pressure is maintained in the container after introduction of WFI.

FIGS. 4A to 4E illustrate, for different initial pressures within the container, the reconstitution times of a lyophilized formulation of a PEGylated fragment of an antibody (certolizumab pegol) with WFI as a function of the time during which the resulting pressure is maintained in the container after introduction of WFI.

Figure 5:
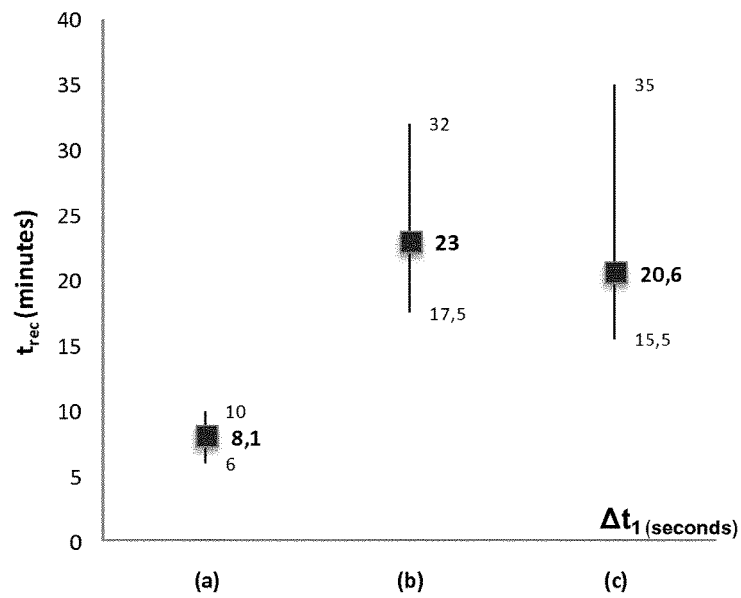

FIG. 5 illustrates the comparison between the reconstitution time of a lyophilized formulation of a PEGylated fragment of an antibody (certolizumab pegol) with WFI:
  (a) a reconstitution process according to the invention as described in Example 3;

(b) a reconstitution process where the resulting vacuum is maintained through solvent introduction and swirling until reconstitution is complete, according to US 2011/0155620;

(c) a reconstitution process in accordance with the instructions for use provided in the packaging.

FIG. 6A shows the three vials of certolizumab pegol (Cimzia®) prior to reconstitution. The vials where then reconstituted according to the three reconstitution processes described in FIG. 5: (a)—left vial—, (b)—central vial—, (c)—right vial—.

FIGS. 6B, 6C, 6D, 6E, and 6F illustrate the visual aspects of the vial contents at different times during the reconstitution process according to process (a)—left vial—, (b)—central vial—, and (c)—right vial—as described in FIG. 5.

DETAILED DESCRIPTION OF THE INVENTION

The problems identified in the background section have herein been solved by the provision of a new process for the reconstitution of a solid form of a pharmaceutical composition.

As such, in a first embodiment the present invention relates to a process for the reconstitution of a solid form of a pharmaceutical composition, comprising the following successive steps:

(i) providing the solid form of the pharmaceutical composition in a sealed container, the pressure within the container being an initial pressure $p_i$;

(ii) at a first time point $t_0$, introducing the solvent into said sealed container and maintaining the resulting pressure $p_r$ within the container during a controlled time $\Delta t_1$; and (iii) at a second time point $t_2$, increasing the pressure within the container to a controlled pressure $p_2$ higher than the said resulting pressure $p_r$, until complete reconstitution.

As used herein the term "reconstitution" or "reconstitution of a solid form of a pharmaceutical composition" refers to converting the solid form of the pharmaceutical composition to a liquid state by adding a solvent.

As used herein "reconstitution time" refers to the time it takes for the solid pharmaceutical composition to undergo reconstitution with the solvent, as defined above.

As used herein the term "solid form" of a pharmaceutical composition is: a powder, a spray-dried composition, or a lyophilized (or freeze-dried) composition.

As used herein "complete reconstitution" refers to a state wherein 90%, or alternatively 95%, 96%, 97%, 98%, 99%, 99.5% or 99.9% of the pharmaceutical composition in the container is in liquid state.

As used herein "container" refers to an item used to contain, store, transport or otherwise dispose of the pharmaceutical composition. A type of container widely used in the pharmaceutical industry is a vial, although a skilled artisan would be able to provide other means suitable for such purposes.

As used herein the term "solvent" is a substance that dissolves a solute resulting in a solution. Suitable solvents include for example, water for injection (WFI) which is widely used as a solvent for reconstituting pharmaceutical compositions. However, the solvent may comprise suitable buffered solutions commonly used for injectable solutions such as, but not limited to, phosphate, histidine, acetate, citrate, succinate or lactate buffers. In other cases a buffer may not be necessary and saline solution or for example, 5% dextrose solution, normal saline, and bacteriostatic water are also common solvents used in the art.

Generally, the container containing the solid form of a pharmaceutical composition is tightly closed to maintain sterility of the pharmaceutical composition during storage or shipment. For example, a vial is often closed by a septum and sealed with a crimp. In one embodiment of the invention the solvent for reconstituting the pharmaceutical composition is injected with a needle or spike which is pierced through the septum. Alternatively, any other way of introducing the solvent without substantially affecting the pressure within the container can also be employed such as vial adapters and/or combined syringe adapters including stopcocks or appropriate valves, or other means known to a skilled artisan.

According to a particular embodiment, the initial pressure $p_i$ is from 0.5 Pa to $1.2 \times 10^5$ Pa. Alternatively $p_i$ is from $5 \times 10^3$ Pa to $1 \times 10^5$ Pa, from $1 \times 10^4$ Pa to $8 \times 10^4$ Pa, from $2 \times 10^4$ Pa to $7 \times 10^4$ Pa, from $3 \times 10^4$ Pa to $6 \times 10^4$ Pa or from $4 \times 10^4$ Pa to $5 \times 10^4$ Pa. For example, if the solid form is a lyophilized composition, it may be obtained by lyophilization and the pressure within the container may have been set to a given pressure in view of storage of the lyophilized composition. This pressure may be adequate for beginning the process of the invention. Therefore in a particular embodiment of the invention, $p_i$ is comprised from 0.5 Pa to $2 \times 10^4$ Pa, alternatively 0.5 Pa to $1 \times 10^4$ Pa, 10 Pa to $1 \times 10^4$ Pa, from 100 Pa to $1 \times 10^4$ Pa, from 100 Pa to $1 \times 10^3$ Pa, from 100 Pa to $5 \times 10^3$ Pa or from $2 \times 10^3$ Pa to $1 \times 10^4$ Pa or from $5 \times 10^3$ Pa to $1 \times 10^4$ Pa. On other occasions, the container may be set at a higher or lower pressure, therefore in another embodiment $p_i$ is from $3 \times 10^4$ Pa to $6 \times 10^4$ Pa, alternatively from $4 \times 10^4$ Pa to $5.5 \times 10^4$ Pa, or from $4.75 \times 10^4$ Pa to $5.5 \times 10^4$ Pa.

Alternatively, the pressure $p_s$ within the container during its storage may be different from the initial pressure $p_i$ desired for the first step of the reconstitution process. Therefore, in a further embodiment of the invention the pressure within the container is set to the initial pressure $p_i$, prior to beginning the reconstitution process. The pressure within the container can be set, for example by suction or by injecting a volume of air into the container.

The invention is not limited to an initial pressure $p_i$ that is below atmospheric pressure (i.e. approximately $1 \times 10^5$ Pa) but may also be applied to a solid pharmaceutical composition enclosed in a container in which the initial pressure is atmospheric or above $1 \times 10^5$ Pa.

As a result of the introduction of a certain volume of solvent into the container, the pressure within the container may vary slightly. In particular, since the gas volume is reduced, the resulting pressure $p_r$ tends to increase with respect to $p_i$ and the potential outgassing of said introduced solvent may itself further increase resulting pressure with respect to $p_i$.

Said resulting pressure $p_r$ is maintained within the container during a determined time $\Delta t_1$.

This requires maintaining a tight seal of the container during introduction of the solvent.

According to a particular embodiment, the solvent is introduced as a jet directed at the solid form of the pharmaceutical composition.

As used herein the term "jet" refers to a rapid stream of liquid forced out of a small opening such as but not limited to a needle or a spike opening.

According to another embodiment, the solvent is introduced as a jet directed at the wall of the container.

The resulting pressure $p_r$ is maintained during a defined time $\Delta t_1$ after introduction of the solvent, depending on each pharmaceutical composition.

In a specific embodiment of the invention $\Delta t_1$ is from 1 second to 2 minutes, alternatively from 2 seconds to 1.5 minutes or from 1 second to 1 minute, alternatively from 1 second to 50 seconds, alternatively from 15 to 45 seconds, alternatively from 20 to 40 seconds, or from 20 to 30 seconds.

There is an optimal time $\Delta t_1$, which depends on the pharmaceutical composition, that allows drawing solvent into the parts of the solid that are still dry and/or to reduce the volume of trapped air including bubbles due to the relative pressure increase.

Therefore in a particular embodiment of the process of the invention, the controlled time $\Delta t_1$ of step (ii) is determined as corresponding to the minimum of a curve representing the total reconstitution time $t_{rec}$ as a function of the time $\Delta t_1$ during which the resulting pressure is maintained in the container from the introduction of the solvent.

One advantage of the process for reconstitution according to the invention is that, contrary to reconstitution processes known in the art, little or no crown of bubbles remain at the surface of the pharmaceutical composition following reconstitution. Such bubble and/or foam reduction results in increased recovery of useable composition from the container, thus requiring lower starting amounts of the solid form pharmaceutical composition in the container at production for a given retrieval/dose objective.

After this time $\Delta t_1$, the pressure within the container is increased to a pressure $p_2$ that is greater than the above described resulting pressure $p_r$.

For example, if the pressure $p_r$ within the container after introduction of the solvent is below atmospheric pressure, the pressure $p_2$ can then be set to atmospheric pressure.

In a particular embodiment of the present invention $p_2$ is at least $1.5 \times p_i$.

For example, if the initial pressure $p_i$ is roughly slightly below atmospheric pressure such as $0.98 \times 10^5$ Pa and $p_2$ is $1.5 \times 10^5$ Pa, very mild over pressure obtainable with a syringe, then $p_2$ is in excess of $1.5 \times p_i$ in most patient's situation (i.e. assuming local atmospheric pressure of about $1 \times 10^5$ Pa). Alternatively, if the initial pressure $p_i$ is $0.3 \times 10^5$ Pa and $p_2$ is atmospheric pressure, then $p_2$ is in excess of $3 \times p_i$ in most patient's situation (i.e. assuming local atmospheric pressure of about $1 \times 10^5$ Pa). In another example, if the initial pressure $p_i$ is 100 Pa and $p_2$ is atmospheric pressure, then $p_2$ is about $1000 \times p_i$ in most patient's situation (i.e. assuming local atmospheric pressure of about $1 \times 10^5$ Pa). In yet another example, if the initial pressure $p_i$ is 10 Pa which is easily achieved in common pharmaceutical freeze dried containers, and $p_2$ is atmospheric pressure, then $p_2$ is easily about $1 \times 10^4 \times p_i$ in most patient's situation (i.e. assuming local atmospheric pressure of about $1 \times 10^5$ Pa).

This increased pressure $p_2$ is maintained until complete reconstitution of the solid form pharmaceutical composition is achieved.

The reconstituted composition may then be used immediately or stored for a short time in suitable conditions.

Optionally, in another embodiment of the invention the reconstitution process includes a further step of mixing the solvent and the pharmaceutical composition.

Said mixing can promote reconstitution of the pharmaceutical composition with the solvent and may also result in the breakage of additional bubbles. Therefore this additional step can result in a further reduction of reconstitution time and/or reduction of the foamy ring atop and/or reduction of bubbles.

In one particular embodiment of the invention said mixing may be carried out by a fluidic recirculation of the solvent and the pharmaceutical composition. Such a fluidic recirculation means displacement of fluid by suction and discharge of the mixture within the container. This way of mixing is efficient when the viscosity of the mixture is low, such as below 150 centipoises, below 100 centipoises, below 90 centipoises, below 80, 70 or 60 centipoises, preferably below 50 centipoises and/or when solid forms do not clog the fluidic recirculation system.

However, when the viscosity of the mixture is high or when dry aggregates of the solid form make such a fluidic recirculation difficult to implement, instead, the mixing may be efficiently performed by mechanical mixing, such that the mixture is moved and sheared within the container due to the forces of gravity, acceleration or the motion of a foreign object introduced within the container. Therefore in a further alternative embodiment of the invention, the step of mixing the pharmaceutical composition in the solvent is performed by mechanical mixing.

For example, the rotation of the container at a tilted angle from the vertical position, or the swirling of the container, are mechanical mixing methods. The rotation may be continuous or discontinuous.

In a further embodiment of the invention, the step of mixing the solvent and the pharmaceutical composition combines fluidic recirculation and mechanical mixing, said combination being carried out simultaneously and/or separately in any order.

In a particular embodiment, such a mixing step may be carried out after introducing the solvent in the container, before increasing the pressure to $p_2$ within the container. Alternatively, the mixing step may be carried out after the pressure within the container has been increased to $p_2$. In yet another particular embodiment the mixing step may be performed before and after increasing the pressure to $p_2$.

As a person skilled in the art would understand, the steps of the process according to the invention can be performed manually, or alternatively the process may also be performed with the aid of an automated device or system.

In a further embodiment the process according to any of the embodiments of the invention comprises an additional step of further increasing the pressure within the container to a pressure $p_3$ after a defined time at $p_2$ and before complete reconstitution of the pharmaceutical composition.

In one embodiment, if $p_i$ and $p_r$ are below atmospheric pressure, i.e. $1 \times 10^5$ Pa, and $p_2$ is the atmospheric pressure, $p_3$ may be from $1.5 \times 10^5$ Pa to $1.5 \times 10^6$ Pa.

In a particular embodiment of the present invention $p_3$ is at least $1.5 \times p_2$.

In a further embodiment of the invention, in the process according to any of the embodiments of the invention, pressure cycles comprising successive pressure increases and decreases are applied after elevating to pressure $p_2$ and before elevating to pressure $p_3$. Such additional pressure cycles make for the removal of most remaining bubbles and/or foam.

In an additional embodiment of the invention, these pressure cycles are applied simultaneously and/or alternatively with mixing. Indeed, pressure variations and mixing favor bubbles' coalescence and removal.

To further help understanding of the different embodiments of the process according to the present invention, FIGS. 2A to 2D have been included. As a skilled artisan would understand, other time frames are possible, provided that the pressure resulting from the introduction of the solvent is maintained during a defined time $\Delta t_1$ and then increased.

In a particular embodiment of the invention, the solid form pharmaceutical composition to be reconstituted is a lyophilized composition.

In another embodiment said solid form pharmaceutical composition comprises a biological moiety such as a recombinant protein, an antibody or a steroid hormone. In a further particular embodiment said biological moiety comprises a monoclonal antibody, a polyclonal antibody or an antigen-binding fragment thereof.

The term "antibody" or "antibodies" as used herein refers to monoclonal or polyclonal antibodies. The term "antibody" or "antibodies" as used herein includes but is not limited to recombinant antibodies that are generated by recombinant technologies as known in the art. "Antibody" or "antibodies" include antibodies' of any species, in particular of mammalian species; such as human antibodies of any isotype, including IgA1, IgA2, IgD, IgG1, IgG2a, IgG2b, IgG3, IgG4 IgE and IgM and modified variants thereof, non-human primate antibodies, e.g. from chimpanzee, baboon, rhesus or cynomolgus monkey; rodent antibodies, e.g. from mouse, rat or rabbit; goat or horse antibodies; and camelid antibodies (e.g. from camels or llamas such as Nanobodies™) and derivatives thereof; or of bird species such as chicken antibodies or of fish species such as shark antibodies. The term "antibody" or "antibodies" also refers to "chimeric" antibodies in which a first portion of at least one heavy and/or light chain antibody sequence is from a first species and a second portion of the heavy and/or light chain antibody sequence is from a second species. Chimeric antibodies of interest herein include "primatized" antibodies comprising variable domain antigen-binding sequences derived from a non-human primate (e.g. Old World Monkey, such as baboon, rhesus or cynomolgus monkey) and human constant region sequences. "Humanized" antibodies are chimeric antibodies that contain a sequence derived from non-human antibodies. For the most part, humanized antibodies are human antibodies (recipient antibody) in which residues from a hypervariable region of the recipient are replaced by residues from a hypervariable region [or complementarity determining region (CDR)] of a non-human species (donor antibody) such as mouse, rat, rabbit, chicken or non-human primate, having the desired specificity, affinity, and activity. In most instances residues of the human (recipient) antibody outside of the CDR; i.e. in the framework region (FR), are additionally replaced by corresponding non-human residues. Furthermore, humanized antibodies may comprise residues that are not found in the recipient antibody or in the donor antibody. These modifications are made to further refine antibody performance. Humanization reduces the immunogenicity of non-human antibodies in humans, thus facilitating the application of antibodies to the treatment of human disease. Humanized antibodies and several different technologies to generate them are well known in the art. The term "antibody" or "antibodies" also refers to human antibodies, which can be generated as an alternative to humanization. For example, it is possible to produce transgenic animals (e.g., mice) that are capable, upon immunization, of producing a full repertoire of human antibodies in the absence of production of endogenous murine antibodies. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies with specificity against a particular antigen upon immunization of the transgenic animal carrying the human germ-line immunoglobulin genes with said antigen. Technologies for producing such transgenic animals and technologies for isolating and producing the human antibodies from such transgenic animals are known in the art. Alternatively, in the transgenic animal; e.g. mouse, only the immunoglobulin genes coding for the variable regions of the mouse antibody are replaced with corresponding human variable immunoglobulin gene sequences. The mouse germline immunoglobulin genes coding for the antibody constant regions remain unchanged. In this way, the antibody effector functions in the immune system of the transgenic mouse and consequently the B cell development is essentially unchanged, which may lead to an improved antibody response upon antigenic challenge in vivo. Once the genes coding for a particular antibody of interest have been isolated from such transgenic animals the genes coding for the constant regions can be replaced with human constant region genes in order to obtain a fully human antibody. Other methods for obtaining human antibodies/antibody fragments in vitro are based on display technologies such as phage display or ribosome display technology, wherein recombinant DNA libraries are used that are either generated at least in part artificially or from immunoglobulin variable (V) domain gene repertoires of donors. Phage and ribosome display technologies for generating human antibodies are well known in the art. Human antibodies may also be generated from isolated human B cells that are ex vivo immunized with an antigen of interest and subsequently fused to generate hybridomas which can then be screened for the optimal human antibody. The term "antibody" or "antibodies" as used herein, also refers to an aglycosylated antibody.

The term "antibody" or "antibodies" as used herein also refers to an antibody fragment. A fragment of an antibody comprises at least one heavy or light chain immunoglobulin domain as known in the art and binds to an antigen. Examples of antibody fragments according to the invention include Fab, Fab', F(ab')$_2$, and Fv and scFv fragments; as well as diabodies; triabodies; tetrabodies; minibodies; domain antibodies (dAbs), such as sdAbs, VHH and VNAR fragments; single-chain antibodies; bispecific, trispecific, tetraspecific or multispecific antibodies formed from antibody fragments or antibodies, including but not limited to Fab-Fv or Fab-Fv-Fv constructs. Antibody fragments as defined above are known in the art.

In certain embodiments of this invention, the antibodies are antibodies that are modified by covalent attachment of functional moieties such as water-soluble polymers, such as poly(ethyleneglycol), copolymers of poly(ethyleneglycol) and poly(propyleneglycol), carboxymethyl cellulose, dextran, poly(vinylalcohol), poly(vinylpyrrolidone) or poly (proline)—all of which are known to exhibit substantially longer half-lives in blood following intravenous injection than do the corresponding unmodified proteins.

In some embodiments, antibodies of the present invention are antibodies attached to functional moieties such as to poly(ethyleneglycol) (PEG) moieties. In one particular embodiment, the antibody is an antibody fragment and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. Nos. 5,219,996; 5,667,425; WO 98/25971). In another embodiments, a Fab fragment of this invention is modified by the addition to the C-terminal end of its heavy chain one or more amino acids to allow the attachment of a functional moiety. Preferably, the additional amino acids form a modified hinge region containing one or more cysteine residues to which the functional moiety may be attached. Multiple sites can be used to attach two or more PEG molecules.

In certain aspects of this invention, PEG molecules are covalently linked through a thiol group of at least one cysteine residue located in an antibody fragment of this invention. Each PEG molecule attached to the modified antibody fragment may be covalently linked to the sulphur atom of a cysteine residue located in the fragment. The covalent linkage will generally be a disulphide bond or, in particular, a sulphur-carbon bond. Where a thiol group is used as the point of attachment appropriately activated functional moieties, for example thiol selective derivatives such as maleimides and cysteine derivatives may be used. An activated PEG may be used as the starting material in the preparation of PEG-modified antibody fragments as described above. The activated PEG may be any PEG containing a thiol reactive group such as an α-halocarboxylic acid or ester, e.g. iodoacetamide, an imide, e.g. maleimide, a vinyl sulphone or a disulphide. In certain embodiments, an antibody conjugate may comprise two PEG molecules with two maleimide molecules. Starting materials may be obtained commercially or may be prepared from commercially available starting materials using conventional chemical procedures. Particular PEG molecules include 20K methoxy-PEG-amine and M-PEG-SPA.

In one preferred embodiment, an antibody of the invention is a modified Fab fragment which is PEGylated, i.e. has PEG (poly(ethyleneglycol)) covalently attached thereto, e.g. according to the method disclosed in EP 0948544. In one example PEG is attached to a cysteine in the hinge region. In another example, a PEG modified Fab fragment has a maleimide group covalently linked to a single thiol group in a modified hinge region. A lysine residue may be covalently linked to the maleimide group and to each of the amine groups on the lysine residue may be attached a methoxypoly(ethyleneglycol) polymer having a molecular weight of approximately 20,000 Da. The total molecular weight of the PEG attached to the Fab fragment may therefore be approximately 40,000 Da.

In another embodiment, the functional moiety is PEG and is attached using the methods described in WO 98/25971 and WO 04/72116, whereby a lysyl-maleimide group is attached to the cysteine residue at the C-terminal end of the heavy chain, and each amino group of the lysyl residue has covalently linked to it a methoxypoly(ethyleneglycol) residue having a molecular weight of about 20,000 Da. The total molecular weight of the PEG attached to the antibody is therefore approximately 40,000 Da.

In another embodiment, the functional moiety is PEG and is attached to a F(ab)2 fragment using the methods described in WO 98/25971 and WO 04/072116, whereby a lysyl-dimaleimide group is attached to the cysteine residue at the C-terminal end of each Fab heavy chain, and each amino group of the lysyl residue has covalently linked to it a methoxypoly(ethyleneglycol) residue having a molecular weight of about 20,000 Da. The total molecular weight of the PEG attached to the F(ab)2 antibody is therefore approximately 40,000 Da.

In certain embodiments of this invention, the antibody of this invention is a Fab' antibody fragment, which may be fully human or humanized, and is PEGylated either in the heavy chain, the light chain or both. In other embodiments, the antibody fragment, which may be fully human or humanized, is PEGylated on one or both heavy chains, or on one or both light chains, or on both heavy and light chains.

Accordingly, in certain embodiments, an antibody is a PEG-linked antibody (e.g., a PEG-linked human antibody) wherein the PEG is linked to the antibody at a cysteine or at a lysine residue. In certain embodiments, the PEGylated antibody has a hydrodynamic size of at least 24 kD. In other embodiments, the PEG may vary in size from anywhere from 20 to 60 kD (inclusive). In further embodiments, the PEG-linked antibody has a hydrodynamic size of at least 200 kD. In embodiments of the present invention where the antibody is linked to a PEG moiety, the PEGylated antibody may have an increased in vivo half-life relative to an antibody that lacks the PEG moiety.

The term "pegylation," "polyethylene glycol" or "PEG" includes a polyalkylene glycol compound or a derivative thereof, with or without coupling agents or derivatization with coupling or activating moieties (e.g., with thiol, triflate, tresylate, azirdine, oxirane, or preferably with a maleimide moiety, e.g., PEG-maleimide). Other appropriate polyalkylene glycol compounds include, but are not limited to, maleimido monomethoxy PEG, activated PEG polypropylene glycol, but also charged or neutral polymers of the following types: dextran, colominic acids, or other carbohydrate based polymers, polymers of amino acids, and biotin and other affinity reagent derivatives.

Other functional moieties that may be useful in improving the integrity and longevity of the antibodies of the present invention in vivo include polypeptides. For example, the antibodies or antibody fragments of this invention may be modified to include a human serum albumin (HSA) polypeptide. Such an antibody conjugate may exhibit increased stabilization and increased serum half-life compared to a non-conjugated antibody or antigen-binding fragment. For example, in certain embodiments, an antibody conjugated to HSA may exhibit increased in vivo half-life relative to a non-conjugated antibody. The half-life (tα- or tβ-half life) of the HSA-conjugated antibody may be increased by 10%, 20%, 30%, 40%, 50% or more. The tα-half life may be within the range of 0.25 minutes to 12 hours, for example, while the tβ-half life may be within 12-48 hours, for example. The tα- or tβ-half life may preferably be at least 3 days, at least 7 days, at least 14 days, at least 21 days, at least 28 days, least 1 month or more.

In some embodiments of this invention, the antibodies of this invention are antibodies modified with a functional moiety by labeling with a detectable marker, for example, a radioactive isotope, enzyme, dye or biotin, or other affinity reagent.

In some embodiments of this invention, the antibodies of this invention are antibodies modified with a functional moiety by being conjugated to a therapeutic agent, for example, a radioisotope or radionuclide (e.g., 111In or 90Y), toxin moiety (e.g., tetanus toxoid or ricin), toxoid or chemotherapeutic agent (U.S. Pat. No. 6,307,026).

In some embodiments of this invention, the antibodies of this invention are antibodies modified by being conjugated to an imaging agent. Imaging agents may include for example a labeling moiety (e.g., biotin, fluorescent moieties, radioactive moieties, a histidine or myc tag or other peptide tags) for easy isolation or detection.

Further examples of functional moieties for modification of or conjugation antibodies of the invention, may include serotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Functional moieties useful in conjugation include, but are not limited to, anti-folates (e.g. aminopterin and methotrexate), antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins, CC-1065, enedieyenes, neocarzinostatin), and anti-mitotic agents (e.g. vincristine and vinblastine).

Other functional moieties may include chelated radionuclides such as 131I, 111In and 90Y, Lu177, Bismuth213, Californium252, Iridium192 and Tungsten188/Rhenium188, 211astatine; or drugs such as but not limited to, alkylphosphocholines, topoisomerase I inhibitors, taxoids and suramin.

Further functional moieties include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, *pseudomonas* exotoxin, or diphtheria toxin, a maytansinoid (for example, but not limited to, DM1), a protein such as insulin, tumor necrosis factor, α-interferon, β-interferon, nerve growth factor, platelet derived growth factor or tissue plasminogen activator, a thrombotic agent or an anti-angiogenic agent, e.g. angiostatin or endostatin, angiogenin, gelonin, dolstatins, minor groove binders, bis-ido-phenol mustard, or, a biological response modifier such as a lymphokine, interleukin-1 (IL-1), interleukin-2 (IL-2), interleukin-6 (IL-6), granulocyte macrophage colony stimulating factor (GM-CSF), granulocyte colony stimulating factor (G-CSF), nerve growth factor (NGF) or other growth factor.

Other functional moieties may include detectable substances useful, for example, in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions that can be conjugated to antibodies for use as diagnostics. Suitable enzymes include horseradish peroxidase, alkaline phosphatase, beta galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include 125I, 131I, 111In and 99Tc.

As will be shown by the experimental results described below, the process for reconstitution according to the invention is significantly faster as compared to other processes known in the art.

Indeed, in the specific example, the process for reconstitution according to the invention leads to a reconstitution time of about 10 minutes or less, whereas other known processes lead to a reconstitution time in excess of 20 minutes.

EXPERIMENTAL RESULTS

Example 1

Figure 1A:
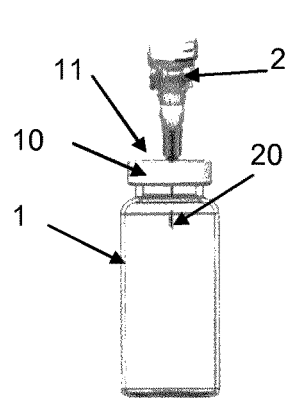
FIGS. 1A to 1C schematically illustrate the setup used to produce the results of Example 1.
Figure 1B:
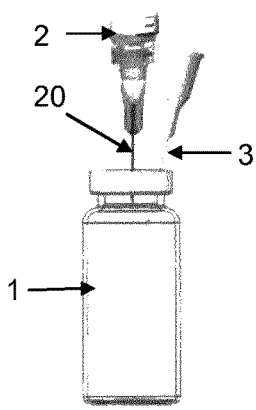
Figure 1C:
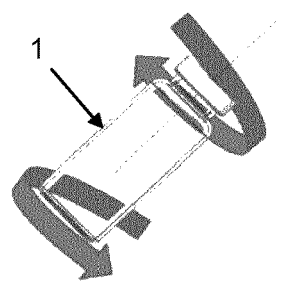

FIGS. 1A-1C exemplify a particular embodiment of the invention wherein the solid form pharmaceutical composition is contained in a vial 1 sealed off with a septum 11 and a metal crimp 10. In this case, as shown in FIG. 1A, the solvent is then introduced using a syringe 2 with a needle 20 attached, wherein the needle 20 passes through the septum 11, the container 1 being in the upright position.

In the example of FIG. 1A referred to above, the solvent can also be injected as a suitable jet, which is obtained by inserting the needle of the syringe containing the solvent straight and deep throughout the septum close to the solid and imparting to the solvent a high pressure to transfer it through the needle to the container at a high velocity. One can then observe the wetted solid during solvent injection as a ring shaped solid, or broken up solid.

In this example, both the initial pressure $p_i$ and resulting pressure $p_r$ after solvent injection are below atmospheric pressure. In this example, after injection of the solvent, the needle and the syringe are kept in the vial to avoid any leak and atmospheric air intake to maintain resulting pressure $p_r$. Therefore as illustrated in FIG. 1B, setting $p_2$ in the container to atmospheric pressure can be done simply by piercing the septum of the container 1 with a hollow needle 3 connected to the atmospheric pressure.

In FIG. 1C, the process according to one of the embodiments of the present invention comprises the additional step of mechanical mixing the solvent with the solid form pharmaceutical composition. In this case the container 1 is tilted to about 45° and rotated along its longitudinal axis. The angle makes for a low shear mixing of the mixture and for the leaching of the wet solution on the dry adherences of solid forms on the container wall, thus recovering more dry form, and consequently improving overall recovery.

Example 2

In this particular case the process of the invention was used to reconstitute lyophilized certolizumab pegol, a PEGylated fragment of an antibody (Fab').

The reconstitution time was reduced to about 10 minutes when the following process was carried out:
  provision of 200 mg of certolizumab pegol in a lyophilized form, available from pharmaceutical manufacturers in a vial at approximately 600 Pa;
  rapid introduction of water for injection (WFI) from a syringe with a 20-gauge needle into the vial in upright position, with the jet directed at the center of the lyophilized cake, without releasing the resulting partial vacuum pressure;
  waiting in upright position;
  releasing the pressure within the vial to atmospheric pressure after 20 to 30 seconds from start of WFI introduction;
  waiting for complete reconstitution with the vial in an upright position.

The term "cake" as used herein means a solid obtained from a lyophilization process in a container.

Example 3

In this particular case the process of the invention was used to reconstitute lyophilized certolizumab pegol, a PEGylated fragment of an antibody (Fab').

The reconstitution time was reduced to an average of 8 minutes and as low as 6 minutes when the following process was carried out:
- provision of 200 mg of certolizumab pegol in a lyophilized form, available from pharmaceutical manufacturers in a vial at approximately 600 Pa;
- rapid introduction of 1 mL water for injection (WFI) from a syringe with a 1-inch 20-gauge needle into the vial in upright position, with the jet directed at the center of the lyophilized cake, without releasing the resulting partial vacuum pressure;
- waiting in upright position;
- releasing the pressure within the vial to atmospheric pressure after 20 to 30 seconds from start of WFI introduction;
- waiting for 20 seconds with the vial in an upright position;
- rotating the vial tilted at 45° at 1 to 2 rev/s until complete reconstitution.

The pharmaceutical composition was considered to be reconstituted once it was fully clear to opalescent or pale yellow, essentially free from solid or poorly wetted or gel portion or particulates in suspension and was monitored by visual glancing through the vial without magnification.

For the current example of certolizumab pegol reconstitution, once WFI was added into the vial, different times $\Delta t_1$ were used before increasing the pressure to atmospheric levels, to determine the optimal time $\Delta t_1$ as described below. Accordingly, the time $\Delta t_1 = 0$ corresponds to a release of vacuum just after solvent introduction. The applicant has noted that the reconstitution time in this case is substantially the same as when the vacuum is released before solvent introduction (see Example 4) but in the latter case more stable bubbles remain at the end of the reconstitution process, resulting in a lower quality of reconstitution.

FIG. 3 shows the determination of the optimal time $\Delta t_1$ during which the pressure $p_r$ resulting from the introduction of the solvent has to be maintained in order to minimize reconstitution time $t_{rec}$ for certolizumab pegol.

As can be evidenced from FIG. 3, the reconstitution time varied as a function of the time $\Delta t_1$ in the form of a U-shape curve.

The minimum of this U-shaped curve defines the optimal time $\Delta t_1$. Although it is not shown here for clarity, $\Delta t_1$ was little impacted by different mixing scenarios. However, it was determined that instead of increasing the pressure strictly at said optimal time, one could increase the pressure after a time $\Delta t_1$ that is comprised between 80 and 120% of this optimal time without significantly deteriorating the reconstitution time.

Example 4

In this particular case the process of the invention was used to reconstitute lyophilized certolizumab pegol, a PEGylated fragment of an antibody (Fab').

The following process was carried out:
- provision of 200 mg of certolizumab pegol in a lyophilized form, available from pharmaceutical manufacturers in a vial at various initial pressure levels;
- rapid introduction of 1 mL of water for injection (WFI) from a syringe with a 1-inch 20-gauge needle into the vial in upright position, with the jet directed at the center of the lyophilized cake, without releasing the resulting partial vacuum pressure; the time reference t=0 is measured immediately after introduction of WFI into the vial;
- once WFI was added into the vial, different times $\Delta t_1$ were used before increasing the pressure to atmospheric levels, to determine the optimal time $\Delta t_1$ as described below;
- rotating the vial gently at 45° angle (about 30 revolutions by hand) for 1 minute so that WFI makes complete contact with the solid cake;
- placing the vial in stationary upright position on a work surface until 2 minutes have elapsed from t=0;
- picking the vial up and rotating it gently for 1 minute again at 45° angle (about 30 revolutions by hand) ensuring that WFI makes contact with the solid material;
- placing the vial in stationary upright position on a work surface until 4 minutes have elapsed from t=0;
- picking the vial up and rotating it gently for 1 minute again at 45° angle (about 30 revolutions by hand) ensuring that WFI makes contact with the solid material; slowly inverting the vial twice (e.g. top to bottom and back again twice);
- placing the vial in stationary upright position on a work surface;
- when 10 minutes have elapsed since t=0, picking the vial up and rotating it gently for approximately 1 minute again at 45° angle (about 30 revolutions by hand) ensuring that WFI makes contact with the solid material; slowly inverting the vial twice (e.g. top to bottom and back again twice);
- placing the vial in stationary upright position on a work surface;
- observing the vial to determine if complete reconstitution has been achieved.

The pharmaceutical composition was considered to be reconstituted once it was fully clear to opalescent or pale yellow, essentially free from solid or poorly wetted or gel portion or particulates in suspension and was monitored by visual glancing through vial without magnification. The time when complete reconstitution is achieved is noted $t_{rec}$.

If at t=15 minutes complete reconstitution has not been achieved, the vial was picked up and rotated gently for 1 minute at 45° angle (about 30 revolutions by hand) ensuring that WFI makes contact with the solid material, and slowly inverted twice (e.g. top to bottom and back again twice); then the vial was placed in stationary upright position on work surface and observed to determine when complete reconstitution has been achieved. If necessary, rotation and inversion were further carried out every 5 minutes until complete reconstitution has been achieved.

FIGS. 4A to 4E show the determination of the optimal time $\Delta t_1$ during which the pressure $p_r$ resulting from the introduction of the solvent has to be maintained in order to minimize reconstitution time $t_{rec}$ for certolizumab pegol, for the following initial pressure in the vial: 3.5 Pa; 650 Pa; 10,000 Pa; 25,000 Pa and 50,000 Pa, respectively.

As can be evidenced from FIGS. 4A to 4E, the reconstitution time varied as a function of the time $\Delta t_1$ in the form of a U-shaped curve for an initial pressure below 25,000 Pa. It can also be observed that the U-shaped curve becomes flatter and the reconstitution time $t_{rec}$ increases as the initial pressure in the vial increases. However, in this example, unlike FIG. 3, $\Delta t_1=0$ data points plotted in FIGS. 4A to 4E correspond to a situation where the vial is first equilibrated at atmospheric pressure just before solvent introduction.

FIG. 5 shows the resulting reconstitution time $t_{rec}$ for lyophilized certolizumab pegol for:
- (a) a reconstitution process as described above in Example 3, according to one embodiment of the invention,
- (b) a reconstitution process known in the art wherein the vial is set at an initial pressure of approximately 600 Pa and without any increase of the pressure within the container after solvent injection and until complete reconstitution. To that end, the needle and the syringe are kept in the vial to avoid any leak before complete reconstitution, and
- (c) a reconstitution process according to the current instructions of use provided from the manufacturer with certolizumab pegol, wherein reconstitution is conducted at the resulting pressure obtained when the solvent is added to the vial against the vial wall and the initial low pressure is partially lost from withdrawal of the needle from the septum prior to swirling operations.

For further clarity, the leaflet provided in the packaging of this lyophilized pharmaceutical composition comprises the following instructions to be executed with the components provided within the delivered packaging (a vial of sterile water for injection, USP (1 mL), single-use plastic syringe, 20 gauge reconstitution needle) using an "appropriate aseptic technique":
- reconstitute lyophilized vial of Cimzia® with 1 mL of sterile water for injection (WFI) with a fresh 20-gauge needle. The sterile WFI should be directed at the vial wall rather than directly on Cimzia®;
- gently swirl vial of Cimzia® for about one minute without shaking, ensuring that all of the powder comes into contact with the sterile WFI. The swirling should be as gentle as possible in order to avoid creating a foaming effect;
- continue swirling every 5 minutes as long as non-dissolved particles are observed. Full reconstitution time may take as long as 30 minutes. The final reconstituted solution should be clear to opalescent, colorless to pale yellow liquid and essentially free from particulates.

Said Cimzia® leaflet stipulates that lyophilized powder should be prepared by a health care professional.

It is clear from the comparison of reconstitution times in FIG. 5 that the reconstitution process (a) according to the invention provided the shortest reconstitution time.

In addition, the variability in reconstitution time was significantly reduced in process (a).

FIGS. 6A-6F show pictures of the visual aspect of three vials used in the present example at different times of the reconstitution process, wherein the left vial was prepared according to process (a), the central vial was prepared according to process (b) and the right vial was prepared according to process (c) as described above.

An efficient wetting was observed when the level of the mixture within the container—which was high just after introduction of the solvent (the volume of the mixture being then considered as the sum of the volume of the solid and the volume of the solvent)—quickly became lower. Indeed, the drop in level shows that the solid has been wet by the solvent, the solvent replacing the voids between the solid particles. The resulting solution may also rapidly look as a milky or bubbly gel, rather than a large lump of dry cake in solvent.

The picture scale of FIG. 6A as compared to FIGS. 6B, 6C, 6D, 6E, 6F has been adjusted so as to view the vials in full.

FIG. 6A shows the three vials just prior to the introduction of the solvent ($t_0$).

In all three cases, the content of the vial has an opaque white color.

FIG. 6B shows the three vials at 1 minute from introduction of the solvent ($t_0+1$ min).

In the case of vial (a) (process according to the invention), the pressure within the vial was released at $\Delta t_1=30$ s.

At the end of this stage, there was a significant difference between the visual aspect of vial (a) compared to vials (b) and (c). In vial (a), the solution already had a translucent aspect, without foam, whereas in vials (b) and (c) a large amount of foam was observed. In vials (b) and (c), aside from the foam, one can see that a large portion of the original lyophilized cake remains unwetted.

FIG. 6C shows the three vials at 4 minutes from introduction of the solvent ($t_0+4$ min).

The solution in vial (a) was substantially transparent and homogeneous in bulk, with only a few medium and large bubbles at the surface of the solution in contact with the wall of the vial. The reconstitution was considered to be mostly completed.

In vials (b) and (c), the solution was mostly translucent, with a significant amount of bubbles at the surface of the solution in contact with the wall of the vial, and large portions of poorly wetted aggregates.

FIG. 6D shows the three vials at 10 minutes from introduction of the solvent ($t_0+10$ min).

The solution in vial (a) is transparent and homogeneous in bulk, with only a few bubbles at the surface of the solution in contact with the wall of the vial. The reconstitution was considered to be completed at $t_0+8$ min at which time vial manipulations such as rotation or swirling ceased. Images for this time point are not included.

In vials (b) and (c), the solution was mainly transparent, but translucent aggregates were in suspension within the solution; in addition, there was still a significant amount of bubbles at the surface of the solution in contact with the wall of the vial. Vial (c) still showed what is considered a foaming ring.

FIG. 6E shows the three vials at 20 minutes from introduction of the solvent ($t_0+20$ min).

The solution in vial (a) is similar to the one of FIG. 6D at 10 minutes from solvent introduction.

In vial (b), the solution was mainly transparent, but translucent aggregates (smaller than in FIG. 6D) could be seen in suspension within the solution and gels were also observed at the bottom of the vial.

In vial (c), the solution was mainly transparent but a translucent aggregate could be seen at the bottom of the vial; in addition, there was still a significant amount of small bubbles at the surface of the solution in contact with the wall of the vial, transiting from a foaming ring to small bubbles. With magnification, it was observed that the bulk of the solution also contained some small bubbles and gels in the bottom of the vial.

FIG. 6F shows the three vials at 25 minutes from introduction of the solvent ($t_0+25$ min).

The solution in vial (a) looked similar to the one of FIG. 6E.

In vial (b), the solution was mainly transparent, but a small translucent aggregate remained visible at the bottom of the vial.

In vial (c), the solution was mainly transparent but a small translucent aggregate could be seen at the bottom of the vial. In addition, there was still a significant amount of small bubbles at the surface of the solution in contact with the wall of the vial.

Interestingly, it can also be noted that in all processes (a) to (c) the volume of solvent introduced in the container was smaller than the volume of solvent removed from the liquid form of the pharmaceutical composition during the lyophilization process.

REFERENCES

[1] Variables Affecting Reconstitution Time of Dry Powder for Injection, Pradip Huwale et al, Pharmaceutical Technology, Jul. 2, 2008
[2] US 2011/0155620
[3] U.S. Pat. No. 5,219,996;
[4] U.S. Pat. No. 5,667,425;
[5] WO 98/25971
[6] EP 0948544
[7] WO 98/25971
[8] WO 04/72116
[9] U.S. Pat. No. 6,307,026
[10] U.S. Pat. No. 4,741,900

The invention claimed is:

1. A process for reconstitution of a solid form of a pharmaceutical composition, comprising the following in succession:
   (i) providing the solid form of the pharmaceutical composition in a sealed container, the pressure within the container being an initial pressure comprised between 0.5 Pa and $1.2 \times 10^5$ Pa;
   (ii) at a first time point, introducing a solvent into said sealed container and maintaining the resulting pressure $p_r$ within the container for a controlled time; and
   (iii) at a second time point, before reconstitution is complete, increasing the pressure within the container to a controlled pressure higher than $p_r$ until complete reconstitution.

2. The process according to claim 1, further comprising, after step (ii) and/or after step (iii), mixing the solvent and the pharmaceutical composition.

3. The process according to claim 2, wherein said mixing is carried out by fluidic recirculation of the solvent and the pharmaceutical composition and/or by mechanical mixing.

4. The process according to claim 3, wherein mechanical mixing of the solvent and the pharmaceutical composition is carried out by rotating the container while the container is tilted with respect to the vertical position.

5. The process according to claim 1, wherein before step (i) the pressure within the container is adjusted to said initial pressure.

6. The process according to claim 1, wherein the initial pressure in the container is from 0.5 Pa to $5 \times 10^4$ Pa.

7. The process according to claim 1, wherein the controlled pressure set in the container at step (iii) is from $1 \times 10^4$ Pa to $1.5 \times 10^6$ Pa.

8. The process according to claim 1, wherein the solid form of the pharmaceutical composition is a lyophilized form of the pharmaceutical composition.

9. The process according to claim 1, wherein the solid form of the pharmaceutical composition is a powder.

10. The process according to claim 1, wherein the solvent is introduced in the container as a jet directed to the solid form of the pharmaceutical composition.

11. The process according to claim 1, further comprising an additional step (iv) wherein after reaching the controlled pressure, the pressure within the container is further increased before complete reconstitution.

12. The process according to claim 1, further comprising an additional step (v) wherein after reaching the controlled pressure, the container is subjected to multiple pressure cycles before complete reconstitution.

13. The process according to claim 1 wherein the initial pressure within the container in step (i) is from 0.5 to $6 \times 10^4$ Pa and the controlled time in step (ii) is from 10 seconds to 2 minutes.

14. The process according to claim 13 further comprising after step (iii) a step of mixing the solvent and the pharmaceutical composition by fluidic recirculation and/or mechanical mixing.

15. A process for minimizing a reconstitution time of a solid form of a pharmaceutical composition, wherein:
   the solid form of the pharmaceutical composition is provided in a sealed container, the pressure within the container being an initial pressure comprised between 0.5 Pa and $1.2 \times 10^5$ Pa;
   at a first time point, a solvent is introduced into said sealed container so that the pressure within the container increases from the initial pressure to a resulting pressure and the resulting pressure is maintained within the container during a non-null controlled time, wherein said controlled time is chosen based on a U-shaped curve representing a total reconstitution time of the pharmaceutical composition as a function of the time during which the resulting pressure is maintained in the container after introduction of the solvent; and
   once said non-null controlled time has elapsed, the pressure is increased within the container to a controlled pressure higher than said resulting pressure.

16. The process of claim 15, wherein before providing the solid form of the pharmaceutical composition in the sealed container, the pressure within the container is adjusted to said initial pressure.

17. The process of claim 15, wherein after reaching the controlled pressure, the pressure within the container is further increased.

18. The process of claim 15, wherein after reaching the controlled pressure, the container is subjected to multiple pressure cycles.

19. The process of claim 15, wherein after reaching the controlled pressure, the solvent and the pharmaceutical composition are mixed by fluidic recirculation and/or mechanical mixing.

* * * * *